United States Patent [19]

Nagarajan et al.

[11] Patent Number: 4,698,327

[45] Date of Patent: Oct. 6, 1987

[54] NOVEL GLYCOPEPTIDE DERIVATIVES

[75] Inventors: Ramakrishnan Nagarajan; Amelia A. Schabel, both of Indianapolis, Ind.

[73] Assignee: Eli Lilly and Company, Indianapolis, Ind.

[21] Appl. No.: 853,583

[22] Filed: Apr. 18, 1986

Related U.S. Application Data

[63] Continuation-in-part of Ser. No. 726,731, Apr. 25, 1985, abandoned.

[51] Int. Cl.$^4$ .................... A61K 35/66; A61K 37/02; C07K 7/50; C07K 9/00
[52] U.S. Cl. ........................................ 514/8; 530/317; 530/322
[58] Field of Search ...................... 514/8; 530/317, 322

[56] References Cited

U.S. PATENT DOCUMENTS

| | | | |
|---|---|---|---|
| 3,067,099 | 12/1962 | McCormick et al. | 167/65 |
| 4,495,179 | 1/1985 | Hoehn et al. | 514/9 |
| 4,547,488 | 10/1985 | Merkel | 514/10 |
| 4,548,925 | 10/1985 | Higgins, Jr. et al. | 514/10 |
| 4,558,008 | 12/1985 | Boeck et al. | 435/75 |

OTHER PUBLICATIONS

Harris et al., "Structure of the Glycopeptide Antibiotic Vancomycin, Evidence for an Asparagine Residue in the Piptide," *J. Am. Chem. Soc.*, 104, 4293–4295 (1982).
Pfeiffer, "Structural Features of Vancomycin," Reviews of Infectious Diseases, vol. 3, Suppl., S205–S209 (Nov.-Dec. 1981).

*Primary Examiner*—Delbert R. Phillips
*Attorney, Agent, or Firm*—Nancy J. Harrison; Leroy Whitaker

[57] ABSTRACT

Novel glycopeptide antibiotics of formula (I) can be prepared from the glycopeptide antibiotics vancomycin, A51568A, A51568B, M43A and M43D by reaction with a ketone or aldehyde followed, if appropriate, by reduction. The new glycopeptide derivatives are useful antibacterial agents.

20 Claims, No Drawings

NOVEL GLYCOPEPTIDE DERIVATIVES

CROSS-REFERENCE TO RELATED APPLICATION

This application is a continuation-in-part of application Ser. No. 726,731, filed Apr. 25, 1985 now abandoned.

SUMMARY OF THE INVENTION

This invention relates to new glycopeptide derivatives of formula (I) which have useful anti-bacterial activity and to methods for preparing these compounds from the glycopeptide antibiotics vancomycin, A515-68A, A51568B, M43A and M43D.

This invention also relates to pharmaceutical formulations containing the formula (I) compounds and to methods of using these compounds as antibacterial agents.

DETAILED DESCRIPTION OF THE INVENTION

New, improved antibiotics are continually in demand, particularly for the treatment of human diseases. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible Many antibiotics, including the glycopeptides, however, have such complex structures that even small changes are difficult to make. Furthermore, it is difficult to predict the effect these changes will make in the desired activity. Processes for modifying known antibiotics and the new active derivatives made by such processes continue, therefore, to be of great importance.

The compounds of the invention are new members of the glycopeptide group of antibiotics. The compounds can be prepared from the known glycopeptides vancomycin (see, for example, U.S. Pat. No. 3,067,099), antibiotic A51568 factor A (see U.S. Pat. No. 4,495,179) and A51568 factor B (see U.S. Pat. No. 4,558,008); antibiotic M43A (see U.S. Pat. No. 4,548,925) and antibiotic M43D (see U.S. Pat. No. 4,547,488).

The compounds of this invention have general formula (I):

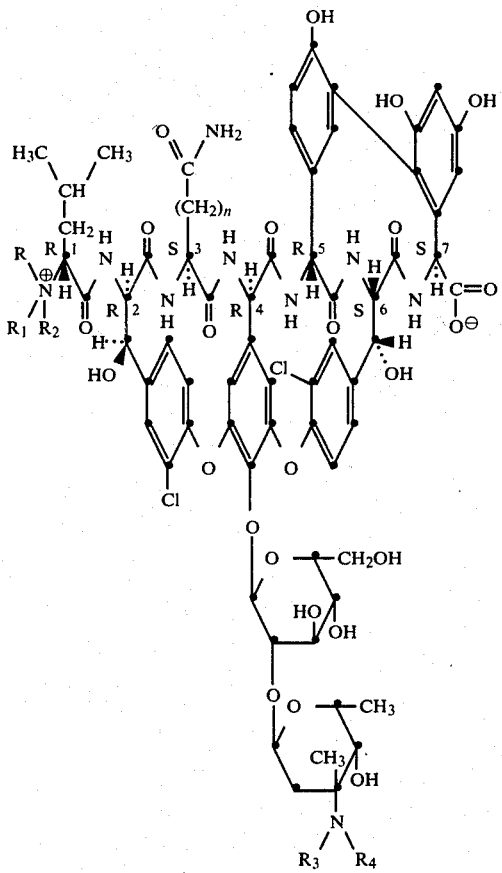

wherein
R is hydrogen or methyl;
n is 1 or 2; and
(i) $R_1$ is hydrogen or methyl;
$R_2$ and $R_3$, independently, are hydrogen or a group of the formula: $R_6R_7CH-$;
$R_6$ and $R_7$ are independently $R_5$, $R_5-(C_1-C_5\text{-alkyl})$ or $R_5-(C_2-C_5\text{-alkenyl})$;
$R_5$ is hydrogen, $C_1-C_{10}$-alkyl, $C_2-C_{10}$-alkenyl, $C_1-C_4$ alkoxy, $C_3-C_{10}$-cycloalkyl, $C_5-C_{12}$-cycloalkenyl, phenyl, napththyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least one atom of the ring system is carbon and at least one atom of the ring system is a heteroatom selected from O, N and S, and $R_5$ may be substituted with one or more hydroxy, nitro, $C_1-C_{10}$-alkoxy, $C_1-C_{10}$-alkyl, phenyl, $C_1-C_6$-alkylthio, nitrile, halo, $C_2-C_4$-acylamino, amino, $C_1-C_4$-dialkylamino groups; and $R_4$ is hydrogen; or
(ii) $R_1$ and $R_2$ and/or $R_3$ and $R_4$ together form a group of the formula

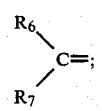

provided that: (1) at least one of $R_2$ and $R_3$ must be other than hydrogen; (2) when n is 2, R must be hydrogen; (3) when R is methyl and $R_3$ is hydrogen, $R_2$ cannot be methyl and (4) when R and $R_1$ are both methyl, then $R_2$ is hydrogen or methyl and n is 1;
and salts of these compounds.

One group of compounds of this invention have formula 1:

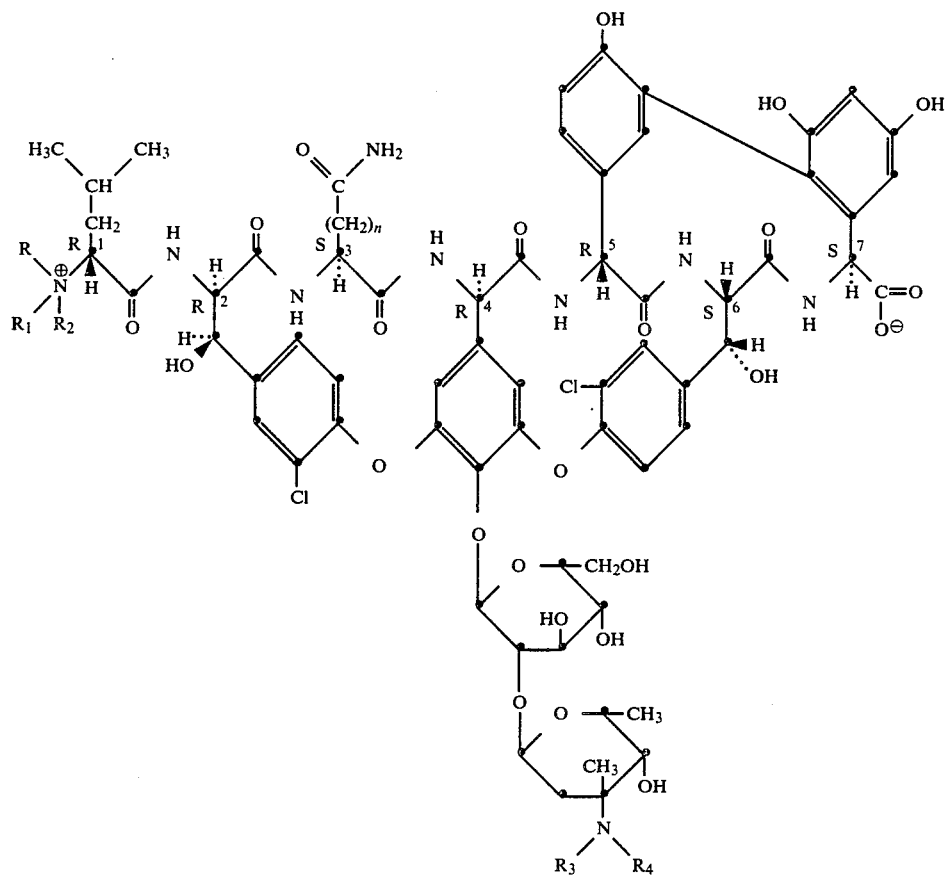

wherein
R is hydrogen or methyl;
$R_1$ is hydrogen;
$R_2$ and $R_3$, independently, are hydrogen, $R_5$—($C_1$-$C_6$)-alkyl or $R_5$—($C_2$-$C_6$-alkenyl); and $R_4$ is hydrogen; or
$R_1$ and $R_2$ or $R_3$ and $R_4$ together form an $R_5$—($C_1$-$C_6$ alkylidenyl) or $R_5$—($C_2$-$C_6$-alkenylidenyl) group;
$R_5$ is $C_1$-$C_{10}$-alkyl, $C_2$-$C_{10}$-alkenyl, $C_3$-$C_{10}$-cycloalkyl, $C_5$-$C_{12}$-cycloalkenyl, phenyl, napththyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least one atom of the ring system is carbon and at least one atom of the ring system is a heteroatom selected from O, N and S, and wherein $R_5$ may be substituted with one or more hydroxy, $C_1$-$C_6$-alkoxy, $C_1$-$C_6$-alkylthio, halo or amino groups; and
n = 1 or 2;
provided that: (1) at least one of $R_2$ and $R_3$ must be other than hydrogen; and (2) when n is 2, R must be hydrogen;
and the salts of these compounds.

Formula (I) compounds in which $R_2$ is an $R_6R_7CH$—group and $R_3$ is hydrogen are preferred.

A second group of compounds of this invention have formula 2:

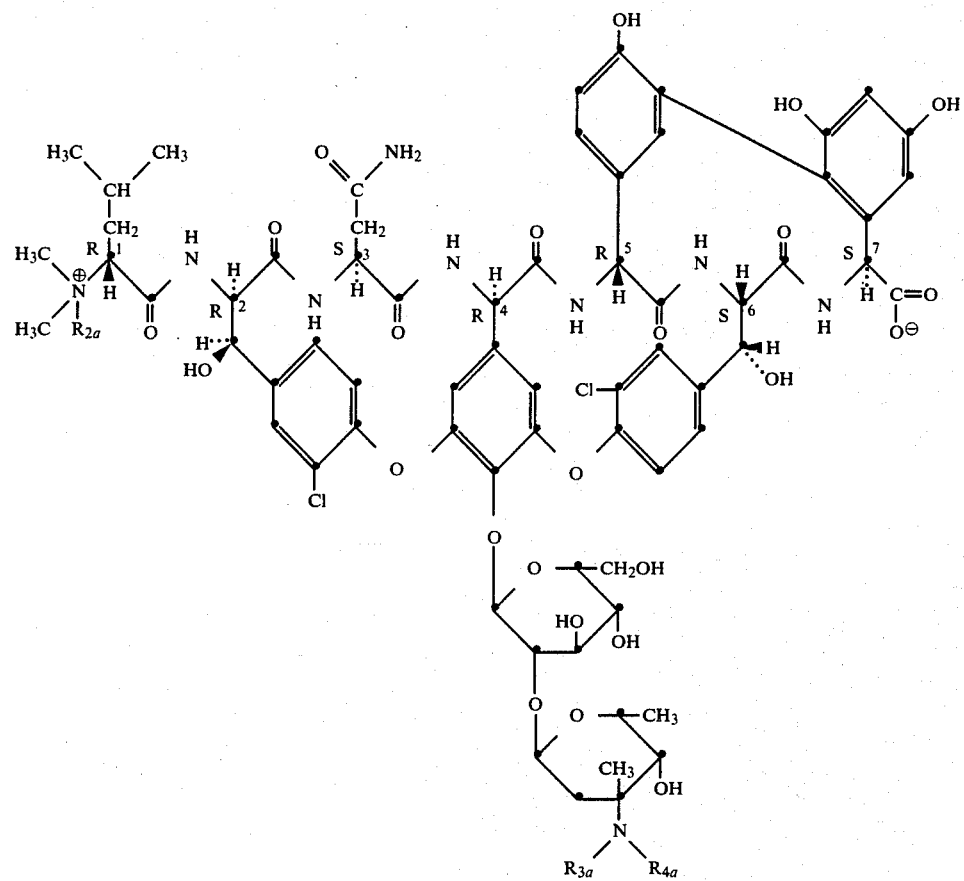

wherein
R$_{2a}$ is hydrogen or methyl;
R$_{3a}$ is R$_5$—(C$_1$-C$_6$-alkyl) or R$_5$—(C$_2$-C$_6$-alkenyl); and
R$_{4a}$ is hydrogen; or R$_{3a}$ and R$_{4a}$ together form an R$_5$—(C$_1$-C$_6$-alkylidenyl) or R$_5$—(C$_2$-C$_6$-alkenylidenyl) group and salts of these compounds.

The compounds of the invention can be prepared by reacting vancomycin, antibiotic A51568 factor A, A51568 factor B, M43A or M43D, which have the following structural formulas

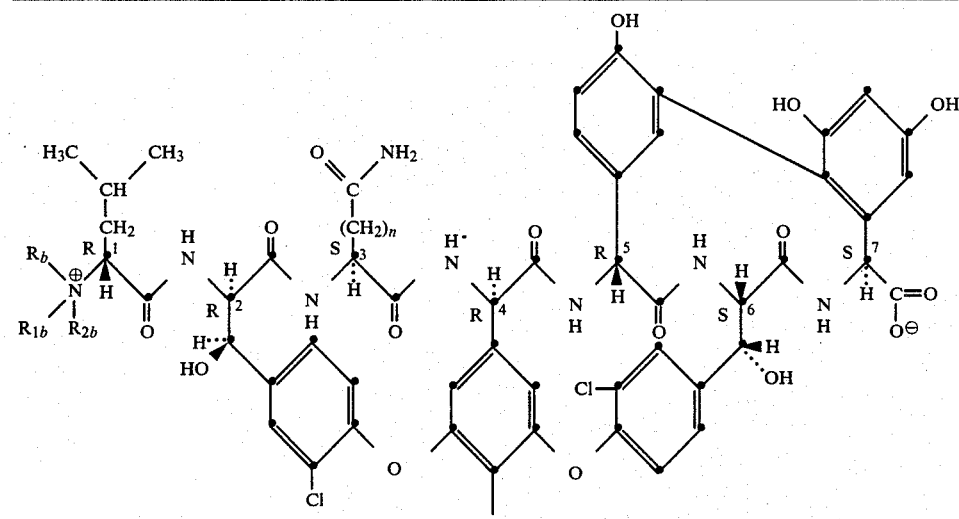

-continued

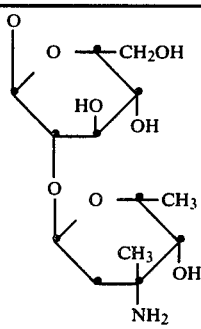

| Compound | $R_b$ | $R_{1b}$ | $R_{2b}$ | n |
|---|---|---|---|---|
| Vancomycin | $CH_3$ | H | H | 1 |
| M43A | $CH_3$ | $CH_3$ | $CH_3$ | 1 |
| M43D | $CH_3$ | $CH_3$ | H | 1 |
| A51568A | H | H | H | 1 |
| A51568B | H | H | H | 2 | with a ketone or aldehyde of formula:

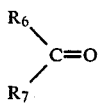

so as to form alkylidene or alkenylidene derivatives of the invention, optionally followed by reduction so as to form alkyl or alkenyl derivatives.

The reaction with the $R^6R^7CO$ compound is preferably carried out at temperatures between 25° and 100° C., preferably from 25° to 70° C., utilizing a polar aprotic solvent such as dimethylformamide.

The reduction of the Schiff's base thus formed can be effected using a chemical reducing agent such as a metal borohydride, for example sodium cyanoborohydride. Once again an aprotic solvent such as dimethylformamide is preferred and the reduction can be effected using temperatures in the range from 25° to 100° C., preferably about 70° C.

It will be appreciated that the sugar groups in the above formulae have the same configuration as do those in vancomycin, i.e., α-O-vancosaminyl-β-O-glucosyl.

Each $R_6$ and $R_7$ group may have from 1 to 15 carbon atoms, and preferably the sum of the carbon atoms in $R_6$ and $R_7$ is no greater than 15. Those compounds wherein either $R_1$ and $R_2$ or $R_3$ and $R_4$ together form an $R_5$—($C_1$–$C_6$-alkylidenyl) or $R_5$—($C_2$–$C_6$-alkenylidenyl) group are known as Schiff bases.

The terms "$C_1$–$C_5$-alkyl", "$C_1$–$C_6$-alkyl" and "$C_1$–$C_{10}$-alkyl" refer to a saturated, straght- or branched-chain alkyl group containing the specified number of carbon atoms. The terms "$C_2$–$C_5$-alkenyl", "$C_2$–$C_6$-alkenyl" and "$C_2$–$C_{10}$-alkenyl" refer to an unsaturated straight or branched-chain alkenyl group containing the specified number of carbon atoms. Those compounds wherein $R_2$ or $R_3$ is $R_5$—($C_1$–$C_6$-alkyl) or $R_5$—($C_2$–$C_6$-alkenyl), referred to herein as "reduced Schiff bases", are prepared by reduction of the corresponding compounds wherein either $R_1$ and $R_2$ or $R_3$ and $R_4$ represent an $R_5$—($C_1$–$C_6$-alkylidenyl) or $R_5$—($C_2$–$C_6$-alkenylidenyl) group.

Methoxy, ethoxy and tert-butoxy are typical $C_1$–$C_6$-alkoxy groups. Methylthio, n-propylthio and isopentylthio are typical $C_1$–$C_6$-alkylthio groups. Halo substituents are selected from the group consisting of chloro, bromo, fluoro and iodo. Cyclopropyl, cycloheptyl and cyclohexadienyl are examples of $C_3$–$C_{10}$-cycloalkyl and $C_5$–$C_{12}$-cycloalkenyl groups.

The formula 1 compounds can be prepared from the antibiotics vancomycin, A51568A and A51568B. The formula 2 compounds can be prepared from the antibiotics M43A and M43D.

The compounds of the invention are shown as zwitterions. Those in the art will recognize, however, that each has a carboxyl group, one or two amino groups and three phenolic groups which can react to form various salts. All such forms of the compounds are part of this invention. The salts are useful, for example, for separating and purifying the antibiotics. In addition, the salts have an improved solubility in water.

The salts are prepared using standard procedures for salt preparation. For example, the zwitterion can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts are an especially preferred group of salts of this invention.

This invention further relates to processes for preparing the compounds of the invention from the glycopeptide antibiotics vancomycin, A51568A, A51568B, M43A and M43D. For convenience in discussing the processes of this invention, the following subgroups are designated:

| Compounds | Definition |
|---|---|
| 1a | 1 compounds wherein $R_1$ and $R_2$ or $R_3$ and $R_4$ together form an $R_5$—($C_1$—$C_6$—alkylidenyl) or $R_5$—($C_2$—$C_6$—alkenylidenyl) group |
| 1b | 1 compounds wherein $R_2$ or $R_3$ is $R_5$—($C_1$—$C_6$—alkyl) or $R_5$—($C_2$—$C_6$—alkenyl) |
| 2a | 2 compounds wherein $R_{3a}$ and $R_{4a}$ together form an $R_5$—($C_1$—$C_6$—alkylidenyl) or $R_5$—($C_2$—$C_6$—alkenylidenyl) group |

| Compounds | Definition |
|---|---|
| 2b | 2 compounds wherein $R_{3a}$ is $R_5$—($C_1$–$C_6$—alkyl) or $R_5$—($C_2$–$C_6$—alkenyl) |

In one aspect, this invention provides a process for preparing a formula 1a compound which comprises reacting vancomycin, A51568A or A51568B with the corresponding

aldehyde or ketone wherein $R_6$ and $R_7$ are as defined, supra, preferably, in a polar aprotic solvent until the 1a compound is formed. A preferred temperature range for this process is from about 25° to about 70° C., and a preferred time is from about 3 to about 18 hours.

In a second aspect, this invention provides a process for preparing a formula 1b compound which comprises reacting the corresponding formula 1a compound with a reducing agent to reduce the $R_6R_7C=N-$ double bond(s) in the 1a compound. A preferred reducing agent for this process is a borohydride such as, for example, sodium cyanoborohydride.

In another aspect, this invention provides a process for preparing a formula 2a compound which comprises reacting M43A or M43D with the corresponding

aldehyde or ketone in a polar aprotic solvent unit the 2a compound is formed. A preferred temperature range for this process is from about 25° to about 70° C., and a preferred time is from about 2 to about 18 hours.

In yet another aspect, this invention provides a process for preparing a formula 2b compound which comprises reacting the corresponding formula 2a compound with a reducing agent to reduce the $R_6R_7C=N-$double bond in the formula 2a compound. A preferred reducing agent for this process is a borohydride such as, for example, sodium cyanoborohydride.

When preparing those formula 1b and 2b compounds wherein the $R_2$, $R_3$, or $R_{3a}$ group contains a —C=C— group, the reducing agent used should be one which selectively reduces the $R_6R_7C=N-$ group only. Sodium borohydride is an example of such a selective reducing agent.

The compounds of this invention are useful antibacterial agents. The formula 1b and 2b compounds are preferred for this purpose.

The formula 1b compounds wherein $R_2$ is hydrogen and $R_3$ is an $R_5$—($C_1$–$C_6$-alkyl) or $R_5$—($C_2$–$C_6$-alkenyl) group are especially useful. Within this group, those compounds wherein the $R_3$ moiety contains from eight to twelve carbon atoms are particularly beneficial.

The formula 1b compounds wherein R is methyl, $R_2$ is hydrogen and $R_3$ is an $R_5$—($C_1$–$C_6$-alkyl or $R_5$—($C_2$–$C_6$-alkenyl) group are more readily and inexpensively prepared since the starting material, vancomycin, is a commercial product.

Another useful group of formula 1b compounds are those wherein $R_3$ is hydrogen and $R_2$ is an $R_5$—($C_1$–$C_6$-alkyl) or $R_5$—($C_2$–$C_6$-alkenyl) group. Preferred compounds within this group are those wherein the $R_2$ moiety contains from five to fourteen carbon atoms. Economically preferably compounds within this group are those wherein R is methyl (the compounds prepared from vancomycin).

Yet another group of formula 1b compounds are those wherein $R_2$ and $R_3$ are both $R_5$—($C_1$–$C_6$-alkyl) or $R_5$—($C_2$–$C_6$-alkenyl) groups. Again, the most preferred compounds of this subgroup are those wherein R is methyl.

Illustrative compounds of this invention are listed in Tables I–IV.

TABLE I

Illustrative Formula 1b Compounds[a]

| Compound No. | R | $R_2$ | $R_3$ |
|---|---|---|---|
| 1 | Me | H | n-dodecyl |
| 2 | Me | H | n-decyl |
| 3 | Me | n-decyl | H |
| 4 | Me | n-decyl | n-decyl |
| 5 | Me | H | n-nonyl |
| 6 | Me | n-nonyl | n-nonyl |
| 7 | Me | H | n-octyl |
| 8 | Me | n-octyl | H |
| 9 | Me | n-octyl | n-octyl |
| 10 | Me | H | n-heptyl |
| 11 | Me | n-heptyl | H |
| 12 | Me | n-heptyl | n-heptyl |
| 13 | Me | H | n-hexyl |
| 14 | Me | n-hexyl | H |
| 15 | Me | H | n-pentyl |
| 16 | Me | n-pentyl | H |
| 17 | Me | H | n-butyl |
| 18 | Me | n-butyl | H |
| 19 | Me | n-butyl | n-butyl |
| 20 | Me | H | n-propyl |
| 21 | Me | n-propyl | H |
| 22 | Me | n-propyl | n-propyl |
| 23 | Me | Et | H |
| 24 | Me | Et | Et |
| 25 | H | n-decyl | H |
| 26 | H | H | n-decyl |
| 27 | H | isooctyl | H |
| 28 | Me | Me | Me |
| 29 | Me | isopropyl | isopropyl |
| 30 | Me | H | isopropyl |
| 31 | Me | H | 5-hydroxy-n-pentyl |
| 32 | Me | 5-hydroxy-n-pentyl | H |
| 33 | Me | " | 5-hydroxy-n-pentyl |
| 34 | Me | H | 6-bromo-n-hexyl |
| 35 | Me | 6-bromo-n-hexyl | H |
| 36 | Me | H | 3-ethoxy-n-propyl |
| 37 | Me | 3-ethoxy-n-propyl | H |
| 38 | Me | 3-ethoxy-n-propyl | 3-ethoxy-n-propyl |
| 39 | Me | H | benzyl |
| 40 | Me | benzyl | H |
| 41 | Me | benzyl | benzyl |
| 42 | H | H | benzyl |
| 43 | Me | H | 3-phenyl-n-(prop-2-enyl) |
| 44 | Me | 3-phenyl-n-(prop-2-enyl) | H |
| 45 | Me | H | 3-phenyl-n-propyl |
| 46 | Me | H | (pyrid-3-yl)methyl |
| 47 | Me | (pyrid-2-yl)methyl | H |
| 48 | Me | H | (2-amino-thiazol-4-yl)ethyl |
| 49 | H | H | phenethyl |
| 50 | Me | H | (indol-3-yl)methyl |
| 51 | Me | H | (adamant-1-yl)methyl |
| 52 | Me | H | n-undecyl |
| 53 | Me | H | 3-(methylthio)-n-propyl |
| 54 | Me | 3-(methylthio)-n-propyl | H |

[a]In these compounds, n = 1 and $R_4$ = H

TABLE II

Illustrative Formula 1a Compounds wherein
$R_1$—$R_2$ = Alkylidenyl or Alkenylidenyl[a]

| Compound No. | R | $R_1$—$R_2$ Group |
|---|---|---|
| 55 | Me | n-decylidenyl |
| 56 | Me | n-nonylidenyl |
| 57 | Me | n-octylidenyl |
| 58 | Me | n-heptylidenyl |
| 59 | Me | n-hexylidenyl |
| 60 | Me | n-pentylidenyl |
| 61 | Me | n-butylidenyl |
| 62 | Me | n-propylidenyl |
| 63 | Me | ethylidenyl |
| 64 | H | n-decylidenyl |
| 65 | Me | isopropylidenyl |
| 66 | Me | 5-hydroxy-n-pentylidenyl |
| 67 | Me | 6-bromo-n-hexylidenyl |
| 68 | Me | 3-ethoxy-n-propylidenyl |
| 69 | Me | benzylidenyl |
| 70 | Me | 3-phenyl-n-(prop-2-enylidenyl) |
| 71 | Me | 3-phenyl-n-propylidenyl |
| 72 | Me | (pyrid-4-yl)methylidenyl |
| 73 | Me | (2-amino-thiazol-4-yl)ethylidenyl |
| 74 | Me | phenethylidenyl |
| 75 | Me | (indol-3-yl)methylidenyl |
| 76 | Me | (adamant-1-yl)methylidenyl |
| 77 | Me | 3-(methylthio)-n-propylidenyl |
| 78 | Me | n-undecylidenyl |

[a]In these compounds, n = 1 and $R_3$ and $R_4$ = H

TABLE III

Illustrative Formula 1a Compounds wherein $R_1$—$R_2$
and $R_3$—$R_4$ = Alkylidenyl or Alkenylidenyl[a]

| Cmpd. No. | R | $R_1$—$R_2$ Group | $R_3$—$R_4$ Group |
|---|---|---|---|
| 79 | Me | n-decylidenyl | n-decylidenyl |
| 80 | Me | n-nonylidenyl | n-nonylidenyl |
| 81 | Me | n-octylidenyl | n-octylidenyl |
| 82 | Me | n-heptylidenyl | n-heptylidenyl |
| 83 | Me | n-butylidenyl | n-butylidenyl |
| 84 | Me | n-propylidenyl | n-propylidenyl |
| 85 | Me | ethylidenyl | ethylidenyl |
| 86 | H | n-decylidenyl | n-decylidenyl |
| 87 | Me | isopropylidenyl | isopropylidenyl |
| 88 | Me | 5-hydroxy-n-pentylidenyl | 5-hydroxy-n-pentylidenyl |
| 89 | Me | 6-bromo-n-hexylidenyl | 6-bromo-n-hexylidenyl |
| 90 | Me | 3-ethoxy-n-propylidenyl | 3-ethoxy-n-propylidenyl |
| 91 | Me | benzylidenyl | benzylidenyl |
| 92 | Me | 3-phenyl-n-(prop-2-enylidenyl) | 3-phenyl-n-(prop-2-enylidenyl) |
| 93 | Me | 3-phenyl-n-propylidenyl | 3-phenyl-n-propylidenyl |
| 94 | Me | (pyrid-4-yl)-methylidenyl | (pyrid-4-yl)-methylidenyl |
| 95 | Me | (2-aminothiazol-4-yl)ethylidenyl | (2-aminothiazol-4-yl)ethylidenyl |
| 96 | Me | phenethylidenyl | phenethylidenyl |
| 97 | Me | (indol-3-yl)-methylidenyl | (indol-3-yl)-methylidenyl |
| 98 | Me | (adamant-1-yl)-methylidenyl | (adamant-1-yl)-methylidenyl |

[a]In these compounds, n = 1

TABLE IV

Illustrative Formula 1a Compounds wherein
$R_3$ and $R_4$ = Alkylidenyl or Alkenylidenyl[a]

| Compound No. | R | $R_3$—$R_4$ Group |
|---|---|---|
| 99 | Me | n-dodecylidenyl |
| 100 | Me | n-decylidenyl |
| 101 | Me | n-nonylidenyl |
| 102 | Me | n-octylidenyl |
| 103 | Me | n-heptylidenyl |
| 104 | Me | n-hexylidenyl |
| 105 | Me | n-pentylidenyl |
| 106 | Me | n-butylidenyl |
| 107 | Me | n-propylidenyl |
| 108 | Me | ethylidenyl |
| 109 | H | n-decylidenyl |
| 110 | Me | isopentylidenyl |
| 111 | Me | 5-hydroxy-n-pentylidenyl |
| 112 | Me | 6-bromo-n-hexylidenyl |
| 113 | Me | 3-ethoxy-n-propylidenyl |
| 114 | Me | benzylidenyl |
| 115 | Me | 3-phenyl-n-(prop-2-enylidenyl) |
| 116 | Me | 3-phenyl-n-propylidenyl |
| 117 | Me | (pyrid-4-yl)methylidenyl |
| 118 | Me | (2-amino-thiazol-4-yl)ethylidenyl |
| 119 | Me | phenethylidenyl |
| 120 | Me | (indol-3-yl)methylidenyl |
| 121 | Me | (adamant-1-yl)methylidenyl |
| 122 | Me | n-undecylidenyl |
| 123 | Me | 3-(methylthio)-n-propylidenyl |

[a]In these compounds, n = 1 and $R_2$ = H

Illustrative formula 2 compounds of this invention are listed in Tables V and VI.

TABLE V

Illustrative Formula 2b Compounds

| Compound No. | $R_{2a}$ | $R_{3a}$ |
|---|---|---|
| 124 | Me | n-decyl |
| 125 | H | n-decyl |
| 126 | Me | n-hexadecyl |
| 127 | Me | isooctyl |
| 128 | Me | n-butyl |
| 129 | Me | benzyl |
| 130 | Me | 5-hydroxypentyl |
| 131 | Me | 3-(methylthio)-n-propyl |
| 132 | Me | 3-phenyl-n-(prop-2-enyl) |
| 133 | H | (pyrid-3-yl)methyl |
| 134 | Me | benzyl |

TABLE VI

Illustrative Formula 2a Compounds

| Compound No. | R | $R_{3a}$—$R_{4a}$ Group |
|---|---|---|
| 135 | Me | n-decylidenyl |
| 136 | H | n-decylidenyl |
| 137 | Me | n-hexadecylidenyl |
| 138 | Me | isooctylidenyl |
| 139 | Me | n-butylidenyl |
| 140 | Me | benzylidenyl |
| 141 | Me | 5-hydroxy-n-pentylidenyl |
| 142 | Me | 3-(methylthio)-n-propylidenyl |
| 143 | Me | 3-phenyl-n-(prop-2-enylidenyl) |
| 144 | H | (pyrid-3-yl)methylidenyl |
| 145 | Me | benzylidenyl |

The formula (I) compounds inhibit the growth of a broad spectrum of pathogenic bacteria, especially Gram-positive bacteria. Tables VII and VIII summarize the minimal inhibitory concentrations (MIC's) at which the compounds inhibit certain organisms, as determined by standard agar-dilution assays.

TABLE VII
In Vitro Activity of Formula (I) Compounds
MIC (mcg/ml)
Compound Number[a]

| Organism | 1 | 2 | 3 | 4 | 5 | 6 | 7 | 8 | 9 | 10 |
|---|---|---|---|---|---|---|---|---|---|---|
| Staphylococcus aureus NRRL B313 | 0.25 | 0.125 | 0.5 | 2 | 0.25 | 1 | 0.25 | 0.5 | 1 | 0.25 |
| Staphylococcus aureus V41 | 0.25 | 0.25 | 0.5 | 4 | 0.25 | 1 | 0.25 | 0.5 | 1 | 0.5 |
| Staphylococcus aureus X400 | 0.25 | 0.25 | 0.5 | 4 | 0.25 | 2 | 0.25 | 1 | 1 | 0.5 |
| Staphylococcus aureus S13E | 0.25 | 0.25 | 0.5 | 4 | 0.25 | 2 | 0.25 | 1 | 1 | 0.5 |
| Staphylococcus epidermidis EPI1 | 0.5 | 0.25 | 2 | 16 | 0.5 | 4 | 1 | 2 | 4 | 2 |
| Staphylococcus epidermidis 222 | 0.125 | 0.25 | 1 | 4 | 0.25 | 2 | 0.5 | 1 | 2 | 1 |
| Streptococcus pyogenes C203 | 0.125 | 0.06 | 0.5 | 2 | 0.125 | 1 | 0.125 | 0.5 | 1 | 0.5 |
| Streptococcus pneumoniae Park 1 | 0.25 | 0.125 | 0.5 | 4 | 0.25 | 2 | 0.125 | 1 | 1 | 0.125 |
| Streptococcus faecium ATCC 9790 | 0.25 | 0.25 | 0.5 | 4 | 0.25 | 2 | 0.25 | 2 | 2 | 0.5 |
| Streptococcus sp. group D 2041 | 0.125 | 0.25 | 1 | 4 | 0.5 | 2 | 0.5 | 2 | 2 | 1 |
| Haemophilus influenzae C.L. | >128 | 128 | 128 | >128 | 64 | >128 | 32 | 128 | >128 | 128 |
| Haemophilus influenzae 76 | >128 | 128 | >128 | >128 | 64 | >128 | 32 | 128 | >128 | 128 |
| Escherichia coli N10 | >128 | >128 | >128 | >128 | >128 | >128 | >128 | >128 | >128 | >128 |
| Escherichia coli EC14 | >128 | >128 | >128 | >128 | >128 | >128 | >128 | >128 | >128 | >128 |
| Escherichia coli TEM | >128 | >128 | >128 | >128 | >128 | >128 | >128 | >128 | >128 | >128 |
| Klebsiella pneumoniae X26 | >128 | >128 | >128 | >128 | >128 | >128 | >128 | >128 | >128 | >128 |
| Klebsiella pneumoniae X68 | >128 | >128 | >128 | >128 | >128 | >128 | >128 | >128 | >128 | >128 |
| Klebsiella pneumoniae KAE | >128 | >128 | >128 | >128 | >128 | >128 | >128 | >128 | >128 | >128 |

| Organism | 12 | 13 | 15 | 17 | 19 | 20 | 22 | 24 | 26 | 124 |
|---|---|---|---|---|---|---|---|---|---|---|
| Staphylococcus aureus NRRL B313 | 0.5 | 0.5 | 0.5 | 1 | 0.5 | 1 | 2 | 1 | 0.25 | 0.5 |
| Staphylococcus aureus V41 | 1 | 1 | 1 | 1 | 1 | 1 | 2 | 1 | 0.25 | 0.5 |
| Staphylococcus aureus X400 | 1 | 1 | 1 | 1 | 1 | 1 | 2 | 2 | 0.25 | 0.5 |
| Staphylococcus aureus S13E | 1 | 0.5 | 1 | 1 | 1 | 1 | 2 | 2 | 0.25 | 0.5 |
| Staphylococcus epidermidis EPI1 | 2 | 2 | 2 | 4 | 2 | 4 | 4 | 2 | 0.5 | 1 |
| Staphylococcus epidermidis 222 | 1 | 1 | 1 | 2 | 1 | 2 | 4 | 2 | 0.25 | 0.5 |
| Streptococcus pyogenes C203 | 0.5 | 0.5 | 0.5 | 1 | 0.5 | 0.5 | 2 | 1 | 0.25 | 0.25 |
| Streptococcus pneumoniae Park 1 | 0.5 | 0.125 | 0.125 | 0.5 | 0.5 | 0.5 | 1 | 1 | 0.25 | 0.5 |
| Streptococcus faecium ATCC 9790 | 1 | 1 | 2 | 2 | 1 | 1 | 2 | 2 | 0.5 | 0.5 |
| Streptococcus sp. group D 2041 | 1 | 1 | 2 | 4 | 2 | 2 | 8 | 4 | 0.5 | 0.5 |
| Haemophilus influenzae C.L. | >128 | 128 | 128 | 128 | >128 | 128 | >128 | <128 | 128 | >64 |
| Haemophilus influenzae 76 | 128 | 128 | 128 | 128 | 128 | 128 | 128 | 128 | 128 | >64 |
| Escherichia coli N10 | >128 | >128 | >128 | >128 | >128 | >128 | >128 | >128 | >128 | >64 |
| Escherichia coli EC14 | >128 | >128 | >128 | >128 | >128 | >128 | >128 | >128 | >128 | >64 |
| Escherichia coli TEM | >128 | >128 | >128 | >128 | >128 | >128 | >128 | >128 | >128 | >64 |
| Klebsiella pneumoniae X26 | >128 | >128 | >128 | >128 | >128 | >128 | >128 | >128 | >128 | >64 |
| Klebsiella pneumoniae X68 | >128 | >128 | >128 | >128 | >128 | >128 | >128 | >128 | >128 | >64 |
| Klebsiella pneumoniae KAE | >128 | >128 | >128 | >128 | >128 | >128 | >128 | >128 | >128 | >64 |

[a]Compound Numbers from Tables I–V

TABLE VIII

In Vitro Activity of Formula (I) Compounds

| | MIC (mcg/ml) Compound Number[a] | | | | | | |
|---|---|---|---|---|---|---|---|
| Organism | 77 | 80 | 81 | 84 | 93 | 94 | 105 |
| Staphylococcus aureus NRRL B313 | 0.25 | 0.25 | 0.06 | 0.125 | 0.5 | 0.25 | 0.5 |
| Staphylococcus aureus V41 | 0.5 | 0.5 | 0.125 | 0.125 | 1 | 0.5 | 0.5 |
| Staphylococcus aureus X400 | 0.5 | 0.25 | 0.125 | 0.125 | 1 | 0.5 | 0.5 |
| Staphylococcus aureus S13E | 0.5 | 0.25 | 0.06 | 0.125 | 0.5 | 0.5 | 0.5 |
| Staphylococcus epidermidis EPI1 | 1 | 1 | 0.25 | 0.25 | 2 | 1 | 1 |
| Staphylococcus epidermidis 222 | 0.5 | 0.5 | 0.125 | 0.25 | 1 | 0.5 | 0.5 |
| Streptococcus pyogenes C203 | 0.25 | 0.25 | 0.06 | 0.06 | 0.25 | 0.25 | 0.5 |
| Streptococcus pneumoniae Park 1 | 0.125 | 0.03 | 0.06 | 0.03 | 0.25 | 0.25 | 0.06 |
| Streptococcus faecium ATCC 9790 | 0.5 | 0.25 | 0.06 | 0.125 | 0.25 | 0.25 | 0.5 |
| Streptococcus sp. group D 2041 | 1 | 1 | 0.25 | 0.25 | 0.5 | 0.25 | 2 |
| Haemophilus influenzae C.L. | 128 | 64 | 32 | 32 | >128 | >128 | 64 |
| Haemophilus influenzae 76 | 128 | 64 | 32 | 64 | >128 | >128 | 64 |
| Escherichia coli N10 | >128 | >128 | >128 | >128 | >128 | >128 | >128 |
| Escherichia coli EC14 | >128 | >128 | >128 | >128 | >128 | >128 | >128 |
| Escherichia coli TEM | >128 | >128 | >128 | >128 | >128 | >128 | >128 |
| Klebsiella pneumoniae X26 | >128 | >128 | >128 | >128 | >128 | >128 | >128 |
| Klebsiella pneumoniae X68 | >128 | >128 | >128 | >128 | >128 | >128 | >128 |
| Klebsiella pneumoniae KAE | >128 | >128 | >128 | >128 | >128 | >128 | >128 |

[a]Compound Numbers = Example Numbers

The compounds of this invention have also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., *J. Bacteriol.* 81, 233–235 (1961)]. $ED_{50}$ values observed are given in Tables IX and X.

TABLE IX

$ED_{50}$ Values for Formula 1 Compounds[a]

| | $ED_{50}$(mg/kg/2) Compound Numbers[b] | | | | | |
|---|---|---|---|---|---|---|
| Organism | 1 | 2 | 3 | 5 | 7 | 8 |
| Staphylococcus aureus | >5 | 1.8 | >5 | 2.9 | 3.4 | >5 |
| Streptococcus pyogenes | 0.31 | 1.6 | 4.6 | 0.56 | 0.98 | 3.7 |
| Streptococcus pneumoniae | 0.42 | 0.51 | 3.6 | 0.81 | 0.44 | 3.1 |

[a]Administered subcutaneously
[b]Compound numbers from Table I

TABLE X

$ED_{50}$ Values for Formula (I) Compounds[a]

| | $ED_{50}$(mg/kg/2) Compound Numbers[b] | | | | | | |
|---|---|---|---|---|---|---|---|
| Organism | 77 | 80 | 81 | 84 | 93 | 94 | 105 |
| Staphylococcus aureus | 1.1 | 1.34 | 0.74 | 0.65 | 0.19 | >0.12 | 0.98 |
| Streptococcus pyogenes | 0.8 | 0.78 | 1.16 | 0.69 | 0.62 | 0.66 | 1.18 |
| Streptococcus pneumoniae | 1.2 | 0.41 | 1.26 | 1.14 | 0.23 | 0.2 | 1.25 |

[a]Administered subcutaneously
[b]Compound numbers = Example Numbers

Pharmaceutical formulations of formula (I) and their pharmaceutically acceptable salts are also part of this invention. Thus, a formula (I) compound, preferably as a pharmaceutically acceptable salt, can be formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like. The compositions comprising a formula (I) compound will contain from about 0.1 to about 90% by weight of the active compound, and more generally from about 10 to about 30%. The compositions may contain common carriers and excipients, such as corn starch or gelatin, lactose, sucrose, microcrystalline cellulose, kaolin, mannitol, dicalcium phosphate, sodium chloride and alginic acid. Disintegrators commonly used in the formulations of this invention include croscarmellose sodium, microcrystalline cellulose, corn starch, sodium starch glycolate and alginic acid. Tablet binders that can be included are acacia, methylcellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring or the like can also be used. It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. Such fluids as, for example, physiological saline, Ringer's solution or 5% dextrose solution can be used.

For intramuscular preparations, a sterile formulation of a suitable soluble salt form of the compound, for example the hydrochloride salt, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of the antibiotic, for example, the hydrochloride salt, formulated in a diluent such as distilled or deionized water, is particularly useful.

Alternatively, the unit dosage form of the antibiotic can be a solution of the antibiotic or preferably a salt thereof in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating infectious diseases, especially those caused by Gram-positive microorganisms, in animals. The animal may be either susceptible to, or infected with, the microorganism. The method comprises administering to the animal an amount of a formula (I) compound or its pharmaceutically acceptable salt which is effective for this purpose. In general an effective amount of a formula (I) compound is a dose between about 0.5 and about 100 mg/kg. A preferred dose is from about 10 to about 60 mg/kg of active compound. A typical daily dose for an adult human is from about 250 mg to about 1.0 g.

In practicing this method, the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggyback method of IV infusion can also be used.

In another embodiment, this invention relates to methods of increasing feed-utilization efficiency in poultry, swine, sheep and cattle, of promoting growth rates in cattle raised for meat production and of enhancing milk production in lactating ruminants. For increasing feed-utilization efficiency and promoting growth, a formula (I) compound is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/ruminant/day) is suggested.

The following examples are provided to illustrate this invention. To simplify discussion, "$N^{van}$" is used to indicate the nitrogen on vancosamine and "$N^{leu}$" is used to indicate the nitrogen in the leucine group. Reactions were followed by analytical high performance liquid chromatography (HPLC) using a Water's Bondapak $C_{18}$ column with a gradient solvent system of $CH_3CN$ and 0.5% triethylamine (pH 3) buffer and detecting with UV at 254 nm.

EXAMPLES 1-2

Preparation of $N^{van}$-(n-Decylidenyl)vancomycin (Compound 100) and $N^{van}$-(n-Decyl)vancomycin (Compound 2)

Vancomycin free base (5 g, 3.58 mmoles) was dissolved in dimethylformamide (DMF, 75 ml). n-Decyl aldehyde (0.7 ml, 3.72 mmoles) was added. The reaction mixture was stirred for 2 hours in a 70° C. oil bath to give $N^{van}$-(n-decylidenyl)vancomycin (Compound 100).

Sodium cyanoborohydride (275 mg, 4.4 mmoles) was added to the solution containing Compound 100. The reaction mixture was stirred for another 2 hours in the oil bath and then was cooled to room temperature and transferred to a Virtis jar. Celite was added until a thick paste formed. The paste was evaporated under vacuum overnight. The powdery residue obtained was stirred with methanol and filtered three times. The methanol filtrates were combined and evaporated to dryness under vacuum. The residue obtained was triturated with diethyl ether. The insoluble residue was dissolved in methanol and filtered, and the filtrate was evaporated to dryness under vacuum.

This product was purified by reversed-phase high performance liquid chromatography (HPLC), using a Water's Prep Pak/500 column, eluting with an acetonitrile-water gradient system and detecting with UV at 280 nm, to give 793.5 mg of $N^{van}$-(n-decyl)vancomycin (Compound 2). The identity of the product was confirmed by fast-atom-bombardment mass spectrometry (FABMS).

EXAMPLES 3-73

The procedure described Examples 1-2 (with the appropriate starting aldehyde) was used to prepare mono-$N^{van}$-, mono-$N^{leu}$- and di-$N^{van}$, $N^{leu}$ derivatives. In general, the smaller the group to be added, the more complex the crude product and the more difficult the isolation. Generally, the major product is the $N^{van}$ derivative. When A51568A is the starting antibiotic, however, the major product is the $N^{leu}$ derivative. Once again the identity of the product was confirmed by fast-atom-bombardment mass spectrometry. The intermediate Schiff's bases were not isolated (ni) but a molecular ion is given in all cases for the reduced alkyl product.

The following compounds were thus prepared:

| Compound | Name |
|---|---|
| 99 | $N^{van}$—(n-dodecylidenyl)vancomycin (ni) |
| 1 | $N^{van}$—(n-dodecyl)vancomycin, $M^+$ = 1615 |
| 79 | $N^{van}$, $N^{leu}$—di(n-decylidenyl)vancomycin (ni) |
| 4 | $N^{van}$, $N^{leu}$—di(n-decyl)vancomycin, $M^+$ = 1727 |
| 55 | $N^{leu}$—(n-decylidenyl)vancomycin (ni) |
| 3 | $N^{leu}$—(n-decyl)vancomycin, $M^+ + 1$ = 1588 |
| 101 | $N^{van}$—(n-nonylidenyl)vancomycin (ni) |
| 5 | $N^{van}$—(n-nonyl)vancomycin, $M^+$ = 1573 |
| 80 | $N^{van}$, $N^{leu}$—di(n-nonylidenyl)vancomycin (ni) |
| 6 | $N^{van}$, $N^{leu}$—di(n-nonyl)vancomycin, $M^+$ = 1700 |
| 102 | $N^{van}$—(n-octylidenyl)vancomycin (ni) |
| 7 | $N^{van}$—(n-octyl)vancomycin, $M^+ + 1$ = 1560 |
| 81 | $N^{van}$, $N^{leu}$—di(n-octylidenyl)vancomycin (ni) |
| 9 | $N^{van}$, $N^{leu}$—di(n-octyl)vancomycin, $M^+$ = 1671 |
| 57 | $N^{leu}$—(n-octylidenyl)vancomycin (ni) |
| 8 | $N^{leu}$—(n-octyl)vancomycin, $M^+ + 1$ = 1560 |
| 103 | $N^{van}$—(n-heptylidenyl)vancomycin (ni) |
| 10 | $N^{van}$—(n-heptyl)vancomycin, $M^+$ = 1545 |
| 82 | $N^{van}$, $N^{leu}$—di(n-heptylidenyl)vancomycin (ni) |
| 12 | $N^{van}$, $N^{leu}$—di(n-heptyl)vancomycin, $M^+ + 1$ = 1643 |
| 58 | $N^{leu}$—(n-heptylidenyl)vancomycin (ni) |
| 11 | $N^{leu}$—(n-heptyl)vancomycin, $M^+$ = 1545 |
| 104 | $N^{van}$—(n-hexylidenyl)vancomycin (ni) |
| 13 | $N^{van}$—(n-hexyl)vancomycin, $M^+$ = 1531 |
| 59 | $N^{leu}$—(n-hexylidenyl)vancomycin (ni) |
| 14 | $N^{leu}$—(n-hexyl)vancomycin, $M^+$ = 1531 |
| 105 | $N^{van}$—(n-pentylidenyl)vancomycin (ni) |
| 15 | $N^{van}$—(n-pentyl)vancomycin, $M^+ 1$ = 1518 |
| 60 | $N^{leu}$—(n-pentylidenyl)vancomycin (ni) |
| 16 | $N^{leu}$—(n-pentyl)vancomycin, $M^+ + 1$ = 1727 |
| 106 | $N^{van}$—(n-butylidenyl)vancomycin (ni) |
| 17 | $N^{van}$—(n-butyl)vancomycin, $M^+$ = 1503 |
| 83 | $N^{van}$, $N^{leu}$—di(n-butylidenyl)vancomycin (ni) |
| 19 | $N^{van}$, $N^{leu}$—di(n-butyl)vancomycin, $M^+ + 1$ = 1560 |
| 61 | $N^{leu}$—(n-butylidenyl)vancomycin (ni) |
| 18 | $N^{leu}$—(n-butyl)vancomycin, $M^+$ = 1503 |
| 107 | $N^{van}$—(n-propylidenyl)vancomycin (ni) |

| Compound | Name |
|---|---|
| 20 | N$^{van}$—(n-propyl)vancomycin, M$^+$ + 1 = 1490 |
| 84 | N$^{van}$, N$^{leu}$—di(n-propylidenyl)vancomycin (ni) |
| 22 | N$^{van}$, N$^{leu}$—di(n-propyl)vancomycin, M$^+$ + 1 = 1532 |
| 62 | N$^{leu}$—(n-propylidenyl)vancomycin (ni) |
| 21 | N$^{leu}$—(n-propyl)vancomycin, M$^+$ + 1 = 1490 |
| 85 | N$^{van}$, N$^{leu}$—di(ethylidenyl)vancomycin (ni) |
| 24 | N$^{van}$, N$^{leu}$—diethylvancomycin, M$^+$ = 1503 |
| 63 | N$^{leu}$—ethylidenylvancomycin (ni) |
| 23 | N$^{leu}$—ethylvancomycin, M$^+$ = 1475 |
| 28 | N$^{van}$, N$^{leu}$—dimethylvancomycin (64% pure), M$^+$ = 1476 |
| 64 | N$^{leu}$—(n-decylidenyl)-A51568A (ni) |
| 25 | N$^{leu}$—(n-decyl)-A51568A, M$^+$ = 1573 |
| 109 | N$^{van}$—(n-decylidenyl)-A51568A (ni) |
| 26 | N$^{van}$—(n-decyl)-A51568A, M$^+$ = 1573 |
| 135 | N$^{van}$—(n-decylidenyl)-M43A (ni) |
| 124 | N$^{van}$—(n-decyl)-M43A, M$^+$ + 1 = 1616 |
| 122 | N$^{van}$—(n-undecylidenyl)vancomycin (ni) |
| 52 | N$^{van}$—(n-undecyl)vancomycin, M$^+$ + 1 = 1602 |
| 113 | N$^{van}$—(3-ethoxy-n-propylidenyl)vancomycin (ni) |
| 36 | N$^{van}$—(3-ethoxy-n-propyl)vancomycin, M$^+$ + 1 = 1534 |
| 68 | N$^{leu}$—(3-ethoxy-n-propylidenyl)vancomycin (ni) |
| 37 | N$^{leu}$—(3-ethoxy-n-propyl)vancomycin, M$^+$ + 1 = 1534 |
| 90 | N$^{van}$,N$^{leu}$—di(3-ethoxy-n-propylidenyl)-vancomycin (ni) |
| 38 | N$^{van}$,N$^{leu}$—di(3-ethoxy-n-propyl)-vancomycin, M$^+$ + 1 = 1619 |
| 111 | N$^{van}$—(5-hydroxy-n-pentylidenyl)-vancomycin (ni) |
| 31 | N$^{van}$—(5-hydroxy-n-pentyl)vancomycin, M$^+$ = 1533 |
| 66 | N$^{leu}$—(5-hydroxy-n-pentylidenyl)-vancomycin (ni) |
| 32 | N$^{leu}$—(5-hydroxy-n-pentyl)vancomycin, M$^+$ = 1533 |
| 88 | N$^{van}$,N$^{leu}$—di(5-hydroxy-n-pentylidenyl)-vancomycin (ni) |
| 33 | N$^{van}$,N$^{leu}$—di(5-hydroxy-n-pentyl)-vancomycin, M$^+$ = 1619 |
| 123 | N$^{van}$—(3-methylthio-n-propylidenyl)-vancomycin (ni) |
| 53 | N$^{van}$—(3-methylthio-n-propyl)vancomycin, M$^+$ = 1536 |
| 77 | N$^{leu}$—(3-methylthio-n-propylidenyl)-vancomycin (ni) |
| 54 | N$^{leu}$—(3-methylthio-n-propyl)vancomycin, M$^+$ = 1536 |

EXAMPLES 74–109

Similarly prepared were the following reduced compounds. Once again, the intemediate Schiff's bases were not isolated.

| Example No. | |
|---|---|
| 74 | N$^{van}$—(cyclohexylmethyl)vancomycin, M$^+$ = 1543 |
| 75 | N$^{leu}$—(cyclohexylmethyl)vancomycin, M$^+$ = 1543 |
| 76 | N$^{van}$,N$^{leu}$—di(cyclohexylmethyl)vancomycin, M$^+$ = 1639 |
| 77 | N$^{van}$(p-diethylaminobenzyl)vancomycin, M$^+$ + 1 = 1609 |
| 78 | N$^{van}$(p-isopropylbenzyl)vancomycin, M$^+$ = 1579 |
| 79 | N$^{van}$—(benzyl)vancomycin, M$^+$ = 1538 |
| 80 | N$^{van}$—(p-bromobenzyl)vancomycin, M$^+$ = 1617 |
| 81 | N$^{van}$—(p-butylbenzyl)vancomycin, M$^+$ + 1 = 1594 |
| 82 | N$^{van}$,N$^{leu}$—(p-butylbenzyl)vancomycin, M$^+$ + 1 = 1740 |
| 83 | N$^{van}$,N$^{leu}$—(p-butoxybenzyl)vancomycin, M$^+$ = 1771 |
| 84 | N$^{van}$—(p-butoxybenzyl)vancomycin, M$^+$ = 1609 |
| 85 | N$^{van}$—(4-pentylbenzyl)vancomycin, M$^+$ + 1 = 1608 |
| 86 | N$^{van}$—(4-pentyloxybenzyl)vancomycin, M$^+$ + 1 = 1624 |
| 87 | N$^{van}$—(pyrrol-2-ylmethyl)vancomycin, M$^+$ + 1 = 1526 |
| 88 | N$^{van}$—(pyridin-2-ylmethyl)vancomycin, M$^+$ = 1538 |
| 89 | N$^{van}$—(furan-2-ylmethyl)vancomycin, (poor spectrum) |
| 90 | N$^{van}$,N$^{leu}$—(p-isopropylbenzyl)vancomycin, M$^+$ = 1711 |
| 91 | N$^{van}$—(p-methylthiobenzyl)vancomycin, M$^+$ = 1583 |
| 92 | N$^{van}$,N$^{leu}$—(p-methylthiobenzyl)vancomycin, M$^+$ = 1583 |
| 93 | N$^{van}$—(p-octylbenzyl)vancomycin M$^+$ + 1 = 1650 |
| 94 | N$^{van}$—(p-octyloxybenzyl)vancomycin, M$^+$ + 1 = 1665 |
| 95 | N$^{van}$—(p-methoxybenzyl)vancomycin, M$^+$ + 1 = 1568 |

| Example No. | |
|---|---|
| 96 | N$^{van}$—(6-nitro-3,4-dimethoxybenzyl)vancomycin, M$^+$ + 1 = 1642 |
| 97 | N$^{leu}$—(6-nitro-3,4-dimethoxybenzyl)vancomycin, M$^+$ + 1 = 1642 |
| 98 | N$^{leu}$—(p-methoxybenzyl)vancomycin (65% pure), M$^+$ + 1 = 1568 |
| 99 | N$^{van}$,N$^{leu}$—(p-methoxybenzyl)vancomycin, M$^+$ + 1 = 1668 |
| 100 | N$^{van}$—(m-bromobenzyl)vancomycin, M$^+$ = 1617 |
| 101 | N$^{van}$—(o-bromobenzyl)vancomycin, M$^+$ = 1617 |
| 102 | N$^{van}$—(p-chlorobenzyl)vancomycin, M$^+$ = 1572 |
| 103 | N$^{van}$—(2,6-dichlorobenzyl)vancomycin, M$^+$ = 1606 |
| 104 | N$^{van}$—(p-acetamidobenzyl)vancomycin, M$^+$ = 1595 |
| 105 | N$^{van}$—(p-hydroxybenzyl)vancomycin, M$^+$ = 1553 |
| 106 | N$^{leu}$—(p-hydroxybenzyl)vancomycin, M$^+$ = 1553 |
| 107 | N$^{van}$,N$^{leu}$—(p-hydroxybenzyl)vancomycin, M$^+$ = 1659 |
| 108 | N$^{van}$—(p-dimethylaminobenzyl)vancomycin, M$^{30}$ + 1 = 1581 |
| 109 | N$^{van}$—(p-cyanobenzyl)vancomycin, M$^+$ + 1 = 1563 |

EXAMPLES 110–133

Using the procedure described in Examples 1–2 (with the appropriate starting aldehyde or ketone), the following compounds can be prepared:

N$^{van}$-(isopropylidenyl)vancomycin

N$^{van}$-(isopropyl)vancomycin

N$^{leu}$-(isopropylidenyl)vancomycin

N$^{leu}$-(isopropyl)vancomycin

N$^{van}$,N$^{leu}$-di(isopopylidenyl)vancomycin

N$^{van}$,N$^{leu}$-di(isopropyl)vancomycin

N$^{van}$,N$^{leu}$-di(n-decylidenyl)-A51568A

N$^{van}$,N$^{leu}$-di(n-decyl)-A51568A

N$^{van}$-(isooctylidenyl)-A51568A

N$^{van}$-(isooctyl)-A51568A

N$^{van}$-(n-decylidenyl)-A51568B

N$^{van}$-(n-decyl)-A51568B

N$^{leu}$-(n-decylidenyl)-A51568B

N$^{leu}$-(n-decyl)-A51568B

N$^{van}$-(n-decylidenyl)-M43D

N$^{van}$-(n-decyl)-M43D

N$^{van}$-(benzylidenyl)vancomycin

N$^{van}$-[3-phenyl-n-(prop-2-enylidenyl)]vancomycin

N$^{van}$-[(adamant-1-yl)methylidenyl]vancomycin

N$^{leu}$-(phenethylidenyl)vancomycin

N$^{van}$-(benzyl)vancomycin

N$^{van}$-(3-phenyl-n-prop-2-enyl)vancomycin

N$^{van}$-[(adamant-1-yl)methyl]vancomycin

N$^{leu}$-phenethylvancomycin

We claim:

1. A compound of formula (I):

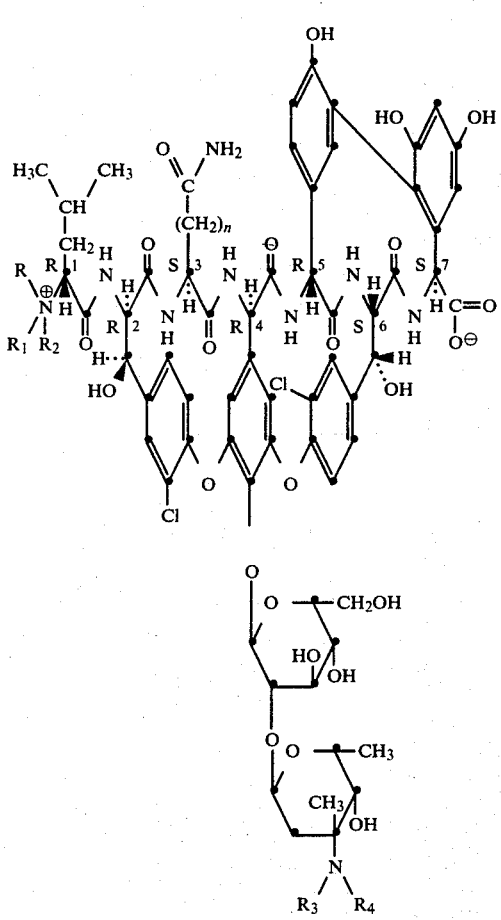

wherein

R is hydrogen or methyl;

n is 1 or 2; and (i) $R_1$ is hydrogen or methyl;

$R_2$ and $R_3$, independently, are hydrogen or a group of the formula: $R_6R_7CH-$;

$R_6$ and $R_7$ are independently $R_5$, $R_5-(C_1-C_5\text{-alkyl})$ or $R_5-(C_2-C_5\text{-alkenyl})$;

$R_5$ is hydrogen, $C_1-C_{10}$-alkyl, $C_2-C_{10}$-alkenyl, $C_1-C_4$ alkoxy, $C_3-C_{10}$-cycloalkyl, $C_5-C_{12}$-cycloalkenyl, phenyl, naphththyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least one atom of the ring system is carbon and at least one atom of the ring system is a heteroatom selected from O, N and S, and $R_5$ may be substituted with one or more hydroxy, nitro, $C_1-C_{10}$-alkoxy, $C_1-C_{10}$ alkyl, phenyl, $C_1-C_6$-alkylthio, nitrile, halo, $C_2-C_4$ acylamino, amino, $C_1-C_4$ dialkylamino groups; and $R_4$ is hydrogen; or (ii) $R_1$ and $R_2$ and/or $R_3$ and $R_4$ together form a group of the formula

provided that: (1) at least one of $R_2$ and $R_3$ must be other than hydrogen; (2) when n is 2, R must be hydrogen; (3) when R is methyl and $R_3$ is hydrogen, $R_2$ cannot be methyl and (4) when R and $R_1$ are both methyl, then $R_2$ is hydrogen or methyl and n is 1;

or a salt thereof.

2. A compound of claim 1 wherein the salt is pharmaceutically acceptable.

3. A compound of claim 1 wherein $R_1$ and $R_2$ or $R_3$ and $R_4$ together form an $R_6R_7C=$ group.

4. A compound of claim 1 wherein $R_2$ or $R_3$ is an $R_6R_7CH-$ group.

5. A compound of claim 4 wherein the group is a $C_1-C_{12}$-alkyl group.

6. A compound of claim 5 wherein the group is a $C_8-C_{10}$-alkyl group.

7. A compound of claim 6 wherein the group is n-decyl.

8. A compound of claim 1 wherein R is methyl.

9. A compound of claim 8 wherein $R_2$ is an $R_6R_7CH-$ group.

10. A compound of claim 9 wherein $R_3$ is hydrogen.

11. A compound of claim 8 wherein $R_3$ is an $R_6R_7CH-$ group.

12. A compound of claim 11 wherein $R_2$ is hydrogen.

13. The compound of claim 8 wherein n is 1, $R_2$ and $R_4$ are hydrogen and $R_3$ is n-decyl.

14. The compound of claim 8 wherein n is 1, $R_3$ and $R_4$ are hydrogen and $R_3$ is benzyl.

15. The compound of claim 8 wherein n is 1, $R_3$ and $R_4$ are hydrogen and $R_3$ is substituted benzyl.

16. A compound of the formula:

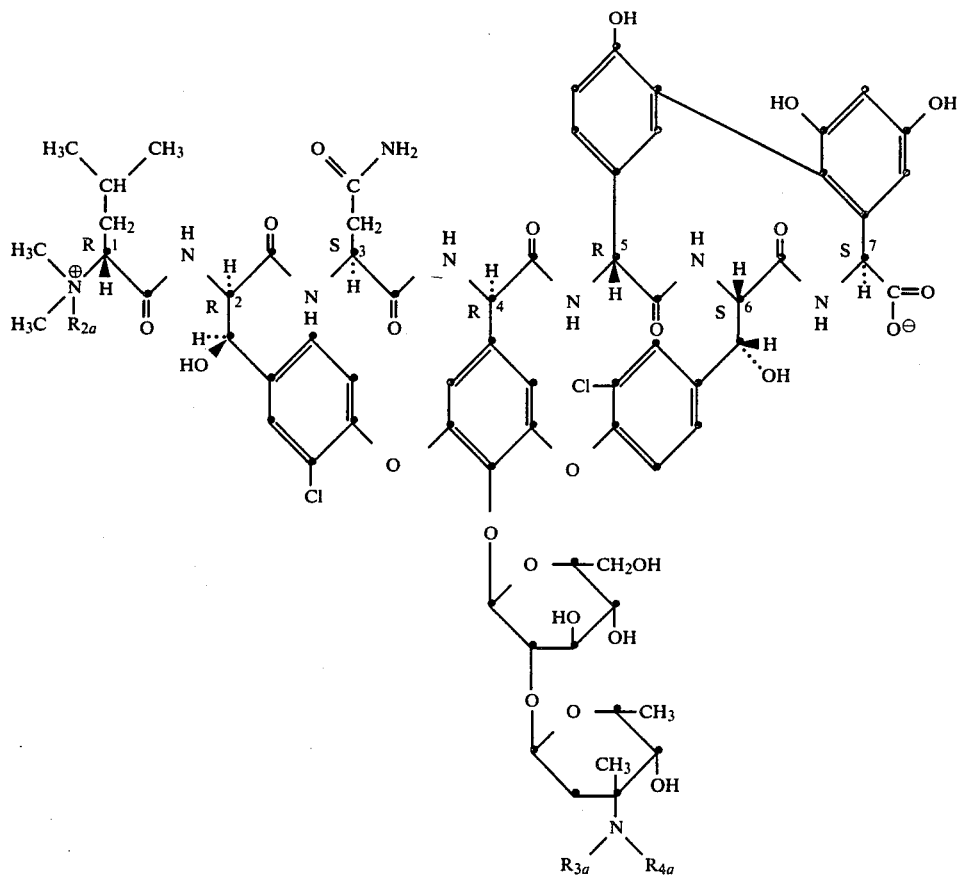

wherein

R$_{2a}$ is hydrogen or methyl;

R$_{3a}$ is R$_5$—(C$_1$-C$_6$-alkyl) or R$_5$—(C$_2$-C$_6$-alkenyl); and

R$_{4a}$ is hydrogen; or

R$_{3a}$ and R$_{4a}$ together form an R$_5$—(C$_1$-C$_6$-alkylidenyl) or R$_5$—(C$_2$-C$_6$-alkenylidenyl) group;

R$_5$ is hydrogen, C$_1$-C$_{10}$-alkyl, C$_2$-C$_{10}$-alkenyl, C$_3$-C$_{10}$-cycloalkyl, C$_5$-C$_{12}$-cycloalkenyl, phenyl, napthyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least one atom of the ring system is carbon and at least one atom of the ring system is a heteroatom selected from O, N and S, and R$_5$ may be substituted with one or more hydroxy, nitro, C$_1$-C$_{10}$-alkoxy, C$_1$-C$_{10}$-alkyl, phenyl, C$_1$-C$_6$-alkylthio, nitrile, halo, C$_2$-C$_4$-acylamino, amino or C$_1$-C$_4$-dialkylamino groups;

or salt thereof.

17. A compound as claimed in claim 1 which is N$^{van}$-(benzyl)vancomycin; N$^{van}$-(p-butylbenzyl)vancomycin; N$^{van}$-(p-butyloxybenzyl)vancomycin; N$^{van}$-(n-decyl)-vancomycin; N$^{van}$-(p-octylbenzyl)vancomycin; or N$^{van}$-(p-octyloxybenzyl)vancomycin.

18. A process for preparing a compound of claim 1 which comprises reacting a compound of the formula

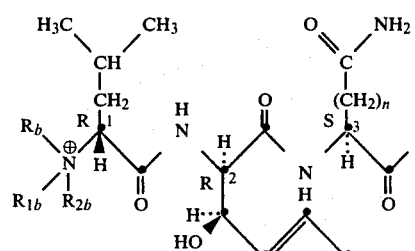
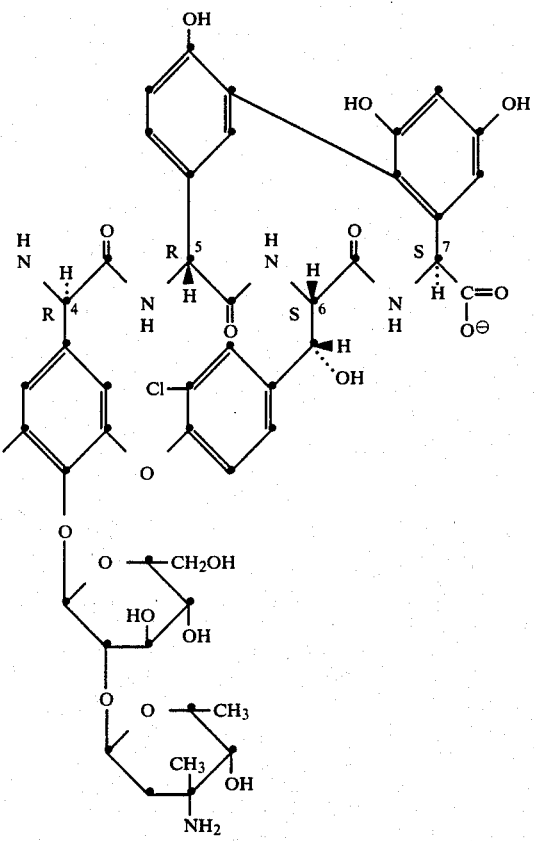

wherein $R_b$, $R_{1b}$ and $R_{2b}$ independently represent hydrogen or methyl, and n is 1 or 2, with a ketone or aldehyde of formula:

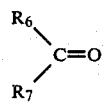

to form an alkylidene or alkenylidene derivative and optionally reducing this derivative to form an alkyl or alkenyl derivative.

19. A pharmaceutical formulation comprising as an active ingredient an effective antibacterial amount of a compound of claim 2 and a pharmaceutically acceptable carrier.

20. A method for treating bacterial infections which comprises administering an effective amount of composition of claim 19 to an animal.

* * * * *